United States Patent [19]

Chernack

[11] Patent Number: 4,867,988
[45] Date of Patent: Sep. 19, 1989

[54] DENTIFRICE CONTAINING MICROENCAPSULATED OXYGEN

[75] Inventor: Milton P. Chernack, West Hempstead, N.Y.

[73] Assignee: Production Previews, Inc., New York, N.Y.

[21] Appl. No.: 35,756

[22] Filed: Apr. 8, 1987

[51] Int. Cl.$^4$ .................. A61K 9/50; A61K 33/40
[52] U.S. Cl. ............................. 424/490; 424/53; 424/616
[58] Field of Search .................. 424/53, 130, 490

[56] References Cited

U.S. PATENT DOCUMENTS

| | | | |
|---|---|---|---|
| 959,605 | 5/1910 | Queisser | 424/130 |
| 2,054,742 | 9/1936 | Elbel | 424/56 |
| 2,120,430 | 6/1938 | Rieche | 424/130 |
| 3,639,574 | 2/1972 | Schmocka | 424/130 |
| 4,020,005 | 4/1977 | Lang | 424/443 |
| 4,277,364 | 7/1981 | Shasha et al. | 424/419 |
| 4,344,857 | 8/1982 | Shasha et al. | 424/419 |
| 4,528,180 | 7/1985 | Schaeffer | 424/130 |
| 4,552,679 | 11/1985 | Schobel et al. | 427/221 |
| 4,557,935 | 12/1985 | Ekenstam et al. | 424/130 |
| 4,671,972 | 6/1987 | Schobel et al. | 427/221 |
| 4,687,663 | 8/1987 | Schaefer et al. | 424/52 |

FOREIGN PATENT DOCUMENTS

| | | | |
|---|---|---|---|
| 432101 | 7/1935 | United Kingdom | 424/130 |
| 632084 | 11/1949 | United Kingdom | 424/130 |

OTHER PUBLICATIONS

Dainippon, GA. 100:183318k (1984).
Dainippon, GA.100:1655282 (1984).
Primer et al., GA.101:193732 (1984).
Hayward et al. GA.103:166126r (1985).
Suzuki et al., (A.10y: 2132220 (1986).
Miller GA.90:109945w (1979).

*Primary Examiner*—Shep K. Rose
*Attorney, Agent, or Firm*—Cohen, Pontani & Lieberman

[57] ABSTRACT

A stable oxygen-containing dentifrice in powder, paste or liquid form which contains a carrier and evenly dispersed therethrough a multiplicity of microencapsulated droplets of an oxygen releasing agent such as hydrogen peroxide. The walls of the microcapsules are rupturable upon mechanical manipulation of the dentifrice as it occurs during the toothbrushing action for releasing the oxygen-containing agent.

12 Claims, No Drawings

DENTIFRICE CONTAINING MICROENCAPSULATED OXYGEN

FIELD OF THE INVENTION

This invention relates to dentifrices having dispersed therein pressure-sensitive microcapsules containing oxygen or an oxygen releasing agent which will be liberated upon mechanical manipulation of the microcapsules. Specifically, the invention relates to a dentifrice containing microencapsulated hydrogen peroxide which will be released during the toothbrushing operation.

BACKGROUND ART

Dentifrice in paste, powder or liquid form is usually used for cleaning or embellishing of teeth. Generally, the dentifrice contains a mixture of a fine, grain-free polishing agent or abrasive for scouring and scrubbing the teeth and which will neutralize potentially deleterious or dangerous acids present in the gaps between the teeth. The latter object is invariably very difficult since bacteria penetrate deeply into the space between the teeth and convert remains of food, mainly sugar and starch, into lactic acid which has a particularly deleterious effect on the dentine.

Although the bacteria destroying effect of oxygen is well know, the incorporation of oxygen or oxygen releasing agents into toothpaste or powders, however, presents various problems. For example, the oxygen is often prematurely released thereby lowering or eliminating the efficacy of the dentrifice in addition to its limiting the shelf life thereof. For this reason the application of hydrogen peroxide separate from and in addition to a toothpaste or powder is often recommended. As used hereinafter the term oxygen containing agent shall include other bactericides and germicides that are non-toxic in the amount, and for the environment and use contemplated herein.

The present invention overcomes these disadvantages by providing a dentifrice containing an oxygen releasing agent such as hydrogen peroxide which is surrounded by envelopes which are rupturable upon mechanical manipulation of the sort occurring during the toothbrushing or cleaning operation.

The technique of microencapsulation per se is known in the art. For example, U.S. Pat. No. 3,686,701 disclosed a cosmetic applicator containing rupturable microcapsules which contain solvents for removal of nail enamel and perfume to mask the odor of said solvents. U.S. Pat. No. 3,691,270 discloses a cosmetic make-up removing composition incorporated in a flexible support throughout which are distributed microcapsules containing the cosmetic make-up removing or treating composition.

SUMMARY OF THE INVENTION

The present invention relates to an oxygen-containing dentifrice which is constituted by a carrier and which has, preferably substantially evenly dispersed there throughout, a multiplicity of microencapsulated particles of an oxygen releasing agent such as hydrogen peroxide or the like. The walls of the microcapsules are rupturable upon mechanical manipulation such as occurs during the toothbrushing operation, for releasing the oxygen at the site where it is most effective.

The process of microencapsulation is well know in the art, does not constitute part of the present invention and is therefore not repeated here. According to one method, the oxygen containing agent is divided into minute particles which are surrounded by rupturable envelopes of suitable material. Any suitable non-toxic material may be selected except that it is critical that the envelopes or microcapsules are not destroyed by the carrier or the remaining components of the dentifrice but withstand any potential chemical or physical attack thereof. It is equally important that the walls of the microcapsules are also not subject to destruction by the oxygen-containing agent which is enveloped by the microcapsules. Thus the envelopes must resist both the action of the carrier which contains all the conventional ingredients of a dentifrice and that of the encapsulated oxygen releasing agent. According to the present invention, the oxygen or oxygen-containing agent is released only upon mechanical manipulation of the microcapsules containing the agent or the oxygen. The walls of the microcapsules are thus rupturable under applied pressure or shear stress when the toothpaste or powder is applied to the bristles of a toothbrush and the brush is thereafter brought in contact with the teeth and gums during the typical toothbrushing operation. Dentifrice, whether in form of a paste, a powder or a liquid, usually contains finely divided grain-free polishing agents or abrasives, stabilizing agents such as aliginates, pectin, gum arabic and the like. If the dentifrice is in the form of a paste, conventional additives include agents such as castor oil, paraffin oil and the like which facilitate the extrusion of the paste from containers. A mixture of the above components with water or glycerine forms a stable paste which does not become dry.

Common additives to a dentifrice also include antiseptic agents, agents which improve the odor and taste of the dentifrice, bicarbonates, and frequently coloring agents.

Other objects, features and advantages of the present invention will become apparent to those skilled in the art from the following detailed description of a preferred embodiment of the invention.

DETAILED DESCRIPTION OF THE PRESENTLY PREFERRED EMBODIMENT

The present invention relates to a dentifrice in the form of a paste, powder or liquid which is stable and releases oxygen at the site and time of greatest effectiveness, namely, at the teeth and gums during toothbrushing operation.

Toothpastes and toothpowders are commonly used for cleansing and embellishment of the teeth. Generally, both toothpastes and toothpowders contain a mixture of the following conventional ingredients. Finely divided, grain-free polishing agents or abrasives such as finely pulverized calcium carbonate (limestone), precipitated limestone, whiting, magnesium carbonate, tricalcium phosphate, dicalcium phosphate, sodium bicarbonate, silica gel and the like. The objective of these agents is to perform a scoring, scrubbing and abrading action to remove food particles and the like. As pointed out, this objective is rather difficult since bacteria penetrate and remain particularly in the space between the teeth where food particles, mainly sugar and starch, are converted into lactic acid which in turn attacks the dentine and is frequently the cause of diseases to the periodontium such as periodontosis and periodontal clasia.

Agents such as water or glycerine or the like aiding in the production of a stable paste which does not dry up easily are frequently added. To further enhance the stability of the paste and to bind the water stabilizing agents such as alginates, pectin, gum arabic, 0.1–0.5% solution of tragacanth and the like are frequently combined with other conventional components making up the dentifrice. In addition, castor oil and paraffin oil are frequently added to impart greater softness to the paste thereby facilitating the discharge thereof from the container.

Other components of dentifrices include agents which enhance the cleansing action such as soaps or 0.5–2% fatty alcohol sulfinates, sodium sulfur ricinoleates and the like. Antiseptic additives include but are not limited to extract of camomile and myrrh, salicylic acid (0.5%), phenyl salicylate (0.5%), chloro thymol (0.1%), thymol (0.5%), boric acid, and the like. These antiseptics exhibit a temporary germicidal effect in the oral cavity and protect the dentifrice from decomposition during storage. It is or course understood that there are many possible and effective compositions of components constituting a multitude of dentifrices. These components are all well known in the art and the compositions or components making up compositions described herein are understood to be exemplary only and not in any sense limiting.

Agents which improve the odor and taste of the dentifrice include but are not limited to peppermint oil, menthol, fennel oil, eucalyptus oil, clove oil and the like, and to enhance the taste of the dentifrice, sugar or saccharin are frequently added. To introduce color, dyes such as carmine red, the red crystalline fluorescent dye eosin, the red acid azo dye amaranth or the like may be added.

Special additives include iodine, bleaching agents such as sodium perborate or potassium chlorate, artificial or natural mineral salts, vitamins such as Vitamins C, D and F, astringents such as tanning agents or aluminum compounds, fluor compounds such as sodium fluoride or calcium fluoride, penicillin to destroy deleterious bacteria, diammonium phosphate and copper chlorophyllin for impeding or inhibiting the growth of acid forming bacteria, tartar removing agents, remineralization salts such as calcium gluconate and enzyme inhibitor or antienzymes such as for example Na-N-lauroyl-sarcosinate, 1,3 dicyclohexylethyl-5-amino-5-methyl pyrimidine which assists to impede or inhibit the formation of acid forming and thus dentine attacking enzymes of bacteria in the mouth for up to twenty-four hours.

Microencapsulation is well known in the art as exemplified by the disclosures of U.S. Pat. Nos. 3,324,500; 3,472,675; 3,598,123; 3,640,629; and the above-mentioned references. Hence, the process of microencapsulation of the oxygen-containing agent does not form part of the present invention separate and distinct from the dental cleansing composition claimed herein. Any suitable known method may be used to divide the oxygen-containing agent into minute liquid particles and to surround the particles by rupturable enveloping walls. Care should however be taken that the material forming the capsules walls is non-toxic and does not otherwise detrimentally affect the gums or other mucous tissue in the oral cavity. Suitable encapsulating or wall-forming materials include, but are not limited to, dextrin, gelatin, gum arabic, casein, paraffin wax, natural waxes such as carnauba wax, bees wax, candelilla wax, Japan wax, acrylic resin, styrene-maleic acid, polyamide, polyethylene, polyethylene-ethyl cellulose mixtures, polyurethanes, polyesters, acetal homopolymers and copolymers, epoxy resins, cellulose acetophthalate and polypropylene.

Thus, any suitable wall material may be used as envelope during the encapsulation process provided the wall-forming material is non-toxic and inert with respect to the action of both, the entrapped oxygen-containing agent as well as the carrier phase or the composition constituting the conventional ingredients of the dentifrice. In addition, the microcapsules must be impermeable to the encapsulated oxygen-containing agent, thus preventing the premature release thereof. The diameter of the microcapsules is not critical to the invention and may range of from about 1 to about 1,000 microns although the average particle size will generally be below 200 microns and preferably of from about 1 to about 100 microns, from about 5 to about 50 microns being presently particularly preferred. Like the diameter, the wall thickness of the microcapsules is also not critical to the invention, but should be of sufficient thickness to withstand normally applied pressure occurring during handling and packing of the composition, but sufficiently thin to allow rupture of the microcapsules by mechanical manipulation thereof.

A particularly preferred oxygen-containing agent is hydrogen peroxide. In the context of the present invention hydrogen peroxide means a diluted solution which, for commercial purposes, is usually composed of 100 parts of water and about 3 parts of hydrogen peroxide. This diluted solution, herein simply termed "hydrogen peroxide", is a clear, odorless, bitter, weakly acidic, non-flammable liquid which in its appearance is not different from water. Prolonged standing causes slow decomposition of the hydrogen peroxide into water and oxygen according to the equation: $2\ H_2O_2 = 2H_2O + O_2$. The decomposition of hydrogen peroxide proceeds more rapid in the presence of bases. For example, in addition to its antiseptic and absorbing effect, the presence of sodium bicarbonate promotes the decomposition of the hydrogen peroxide after its release from the ruptured microcapsules.

In order to prevent the decomposition of the hydrogen peroxide while it is within the microcapsules, small amounts of stabilizers such as urea, salicylic acid, barbituric acid, benzoic acid or the like may be added. Properly stabilized hydrogen peroxide loses only about 1% of its content when kept at room temperature and in darkness.

The various aspects and modifications of the present invention will be further made apparent by reference to the following examples which are understood to be illustrative only and in no way limitative of the present invention. Unless otherwise indicated all amounts refer to parts by weight.

EXAMPLE I

A stable oxygen-containing toothpaste is produced by admixing 20 parts per weight of pure, odorless and tasteless saponaceous powder with 70 parts by weight of water and 70 parts by weight of glycerine.

A solution containing 100 parts of water and about 3 parts of hydrogen peroxide and minute amounts of salicylic acid as stabilizer are divided into minute liquid particles and coated with gum arabic and/or pork gelatin in accordance with any of the known microencapsulated processes. The microcapsules are then introduced into and preferable evenly dispersed throughout the above mixture. A sufficient amount of prepared chalk or whiting is also kneaded into the mixture so that a uniform past is obtained.

EXAMPLE II

A stable oxygen containing toothpaste prepared in accordance with Example I contains 42% precipitated calcium carbonate, 1% traganth, 5% of a mineral salt mixture comprising 44 grams dry sodium sulphate, 2 grams potassium sulphate, 18 grams sodium chloride and 36 grams sodium bicarbonate, and 25% glycerine, 1% peppermint oil and 26% water.

EXAMPLE III

A stable oxygen-containing toothpowder is prepared by admixing 10 grams of peppermint oil with small amounts of prepared chalk or whiting and step by step adding 50 grams orris root, and thereafter adding in small doses a total of 450 grams prepared chalk, 75 grams magnesium carbonate and an effective amount of microencapsulated hydrogen peroxide.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A stable oxygen-containing dentifrice comprising as a carrier a toothpaste containing an effective amount of a base to decompose hydrogen peroxide into water and oxygen; and dispersed there throughout a multiplicity of microencapsulated particles of hydrogen peroxide as an oxygen releasing agent, the walls of said microcapsules being rupturable upon mechanical manipulation for releasing said agent;

said microcapsules being formed by a wall-forming material selected from the group consisting of dextrin, gelatin, gum arabic, casein, paraffin wax, natural waves, acrylic resin, styrene-maleic acid, polyamide, polyethylene, polyethylene-ethyl cellulose mixtures, polyurethanes, polyesters, acetal homopolymers and copolymers, epoxy resins, cellulose acetophthalate and polypropylene;

said microcapsules having a diameter of from about 1 to about 1,000 microns; and the wall thickness of said microcapsules being sufficiently thin to allow rupture by toothbrush action on the toothpaste and sufficiently thick to withstand packing of the composition.

2. The composition of claim 1, wherein the diameter of the microcapsules is below 200 microns.
3. The composition of claim 1, wherein the diameter of the microcapsules is between about 1 to about 100 microns.
4. The composition of claim 1, wherein the diameter of the microcapsules is from about 5 to about 50 microns.
5. The composition of claim 1, wherein the microcapsules additionally contain a stabilizer for stabilizing the oxygen releasing agent.
6. The composition of claim 1, wherein the carrier additionally comprises a polishing agent.
7. The composition of claim 1, wherein the carrier additionally comprises a stabilizer.
8. The composition of claim 1, wherein the carrier additionally comprises a cleansing agent.
9. The composition of claim 1, wherein the carrier additionally comprises an antiseptic.
10. The composition of claim 1, wherein the base is sodium bicarbonate.
11. The composition of claim 1, wherein the carrier contains a coloring agent.
12. The composition of claim 1, wherein the microcapsules are substantially evenly dispersed throughout the carrier.

* * * * *